(12) United States Patent
Chase

(10) Patent No.: US 10,314,933 B2
(45) Date of Patent: Jun. 11, 2019

(54) NETWORK CONTROLLED FRAGRANCE DISPENSING SYSTEM

(71) Applicant: Ambrosia Corporation, Guaynabo, PR (US)

(72) Inventor: Benjamin R. Chase, Highland, UT (US)

(73) Assignee: Ambrosia Corporation, Guaynabo, PR (US)

( * ) Notice: Subject to any disclaimer, the term of this patent is extended or adjusted under 35 U.S.C. 154(b) by 383 days.

(21) Appl. No.: 14/887,924

(22) Filed: Oct. 20, 2015

(65) Prior Publication Data

US 2016/0106875 A1 Apr. 21, 2016

Related U.S. Application Data

(60) Provisional application No. 62/066,720, filed on Oct. 21, 2014.

(51) Int. Cl.
*A61L 9/03* (2006.01)
*A61L 9/12* (2006.01)

(52) U.S. Cl.
CPC .............. *A61L 9/032* (2013.01); *A61L 9/122* (2013.01); *A61L 2209/111* (2013.01)

(58) Field of Classification Search
CPC .................................. A61L 9/032; A61L 9/122
See application file for complete search history.

(56) References Cited

U.S. PATENT DOCUMENTS

| | | | | |
|---|---|---|---|---|
| 2010/0270943 A1* | 10/2010 | Cook | ........................ | A61L 9/03 315/291 |
| 2015/0108241 A1* | 4/2015 | Chase | ........................ | A61L 9/12 239/8 |
| 2015/0373815 A1* | 12/2015 | Patton | ................. | F21V 33/0052 315/297 |
| 2016/0022854 A1* | 1/2016 | Shah | ........................ | A61L 9/03 392/387 |

\* cited by examiner

*Primary Examiner* — Sean E Conley
(74) *Attorney, Agent, or Firm* — Christopher G. Darrow; Darrow Mustafa PC

(57) ABSTRACT

A fragrance dispensing system includes a fragrance dispensing mechanism, a network interface, and a control module. The control module receives a control signal from an input device via the network interface and controls the fragrance dispensing mechanism based on the control signal. The control signal corresponds to settings of the fragrance dispensing mechanism. The fragrance dispensing mechanism may include a fan, a light source, a power save switch, or a combination thereof. A method for controlling a fragrance dispensing system includes generating an interface at an input device, receiving input via the interface, generating a control signal based on the input, and remotely transmitting the control signal to the fragrance dispensing system. The input indicates settings of the fragrance dispensing system. The interface may include a selectable timer option, a selectable power mode, a fan control, a light control, or a combination thereof. The interface may include a fragrance indicator.

13 Claims, 4 Drawing Sheets

NETWORK CONTROLLED FRAGRANCE DISPENSING SYSTEM

RELATED APPLICATION DATA

The present application claims the benefit of priority under 35 U.S.C. § 119 to U.S. Provisional Application No. 62/066,720, filed Oct. 21, 2014, entitled "Network Controlled Fragrance Dispensing System," the disclosure of which is incorporated herein by reference in its entirety.

BACKGROUND

Field of the Disclosure

The present disclosure relates generally to a fragrance dispensing system and, more specifically, to a network controlled fragrance dispensing system.

Description of the Related Art

Fragrance dispensing products may be used to dispense fragrances into surrounding air, thereby "freshening" the air and creating a pleasant atmosphere. In creating the pleasant atmosphere, ambient lighting may also be included as part of a fragrance dispensing product. Examples of types of fragrance dispensing products may include candles, air fresheners, electric fragrance dispensers, scented wax warmers, or the like.

However, the placement of fragrance dispensing products may be limited due to the direct interaction needed with the products. For example, known electric fragrance dispensers may be controlled by a single switch that turns the dispenser on and off. It may be beneficial to provide a fragrance dispenser that can be controlled remotely or according to user-preselected parameters. Furthermore, placement of known fragrance dispensers may be limited to locations having a fixed power source, such as an electrical outlet. It may be beneficial to provide a battery-operated fragrance dispenser that can also be monitored and controlled remotely. Also, known electric fragrance dispensers are limited in the modes of operation available to users. For example, operation may be limited to a single rate of fragrance dispensing. Also for example, a light source may be limited to operation during periods when the fragrance dispenser is actively dispensing fragrances. It may be beneficial to provide a fragrance dispenser that may vary the rate of fragrance dispensing and independently control other features, such as ambient lighting and periods of operation. Other drawbacks and disadvantages of existing fragrance dispensers may also exist.

SUMMARY

The present disclosure is directed to a fragrance dispensing system that addresses the above problems and disadvantages, as well as others.

One embodiment is a fragrance dispensing system comprising a fragrance dispensing mechanism, a network interface, and a control module configured to receive a control signal from an input device via the network interface. The control module controls the fragrance dispensing mechanism based on the control signal. The control signal corresponds to settings of the fragrance dispensing mechanism.

The fragrance dispensing mechanism may include a fan. The control module may determine a fan speed setting based on the control signal. The fragrance dispensing mechanism may include a light source. The control module may determine a light source setting based on the control signal. The light source setting may include a color setting, a light intensity setting, or a combination thereof.

The control module may determine a timer setting based on the control signal. The timer setting may correspond to a time period when the control module controls the fragrance dispensing mechanism.

The fragrance dispensing system may include a power save switch. The control module may determine a power save mode based on a position of the power save switch. The power mode may be selectable between a power save mode and a normal mode.

The control module may actuate airflow for a first duration during the time period and refrain from actuating airflow for a second duration during the time period while in the power save mode.

One embodiment is a method for controlling a fragrance dispensing system. The method includes generating an interface at an input device, receiving input via the interface, generating a control signal based on the input, and remotely transmitting the control signal to the fragrance dispensing system. The input device includes a processor. The input indicates a setting corresponding to a fragrance dispensing system. The fragrance dispensing system is configured to the indicated setting in response to the control signal.

The processor may be a processor of a mobile computing device. The interface may include a selectable timer option corresponding to a timer setting. The receiving input may include receiving an indication of a selection of the selectable timer option. The control signal may include a command to operate according to the timer setting. The interface may include a plurality of selectable options corresponding to a plurality of timer settings. The receiving input may include receiving an indication of a selection of two or more selectable options of the plurality of selectable options. The control signal may include a command to operate according to the timer settings corresponding to the two or more selectable options. Each of the plurality of timer settings may include a set of days and a time period corresponding to an operating state of the fragrance dispensing system.

The fragrance dispensing system may operate according to a selectable power mode while in the operating state. The selectable power mode may be selected from a power saving mode and a normal mode. The fragrance dispensing system may actuate airflow continuously during the time period in the normal mode. The fragrance dispensing system may actuate airflow for a first duration and refrain from actuating airflow for a second duration in the power saving mode. The fragrance dispensing system may cycle between the first duration and the second duration in the power saving mode until the time period has lapsed.

The interface may include a selectable fan speed control option corresponding to a fan speed setting. The receiving input may include receiving an indication of a selection of the selectable fan speed control option. The control signal may include a command to operate according to the fan speed setting.

The interface may include a selectable light source control option corresponding to a light source setting. The receiving input may include receiving an indication of a selection of the selectable light source control option. The control signal may include a command to operate according to the light source setting. The light source control option may include a plurality of color control options corresponding to a plurality of color settings and a light intensity control option corresponding to a light intensity setting. The color setting and the light intensity setting may be part of the light source setting.

The input may indicate a setting corresponding to the fragrance dispensing system and an another setting corresponding to another fragrance dispensing system. The method may include remotely transmitting the control signal to the another fragrance dispensing system. The another fragrance dispensing system may be configured to the indicated another setting in response to the control signal. The interface may include a fragrance indicator representing a fragrance level related to a fragrance device of the fragrance dispensing system.

One embodiment is a fragrance dispensing system comprising a fragrance dispensing mechanism, an interface configured to receive user input, and a control module configured to control the fragrance dispensing mechanism based on the user input. The user input corresponds to settings of the fragrance dispensing mechanism.

The fragrance dispensing mechanism may include a fan and a light source. The user input may correspond to a speed of the fan, a configuration of the light source, and a time period when the control module controls the speed of the fan and the configuration of the light source.

DETAILED DESCRIPTION

Figure 1:
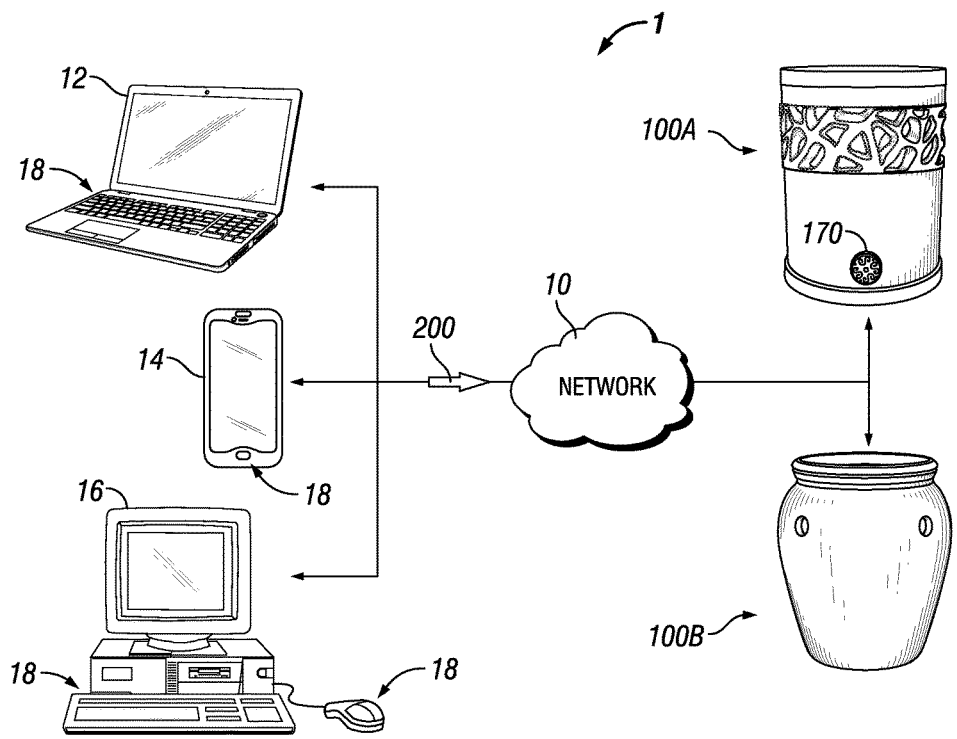
FIG. 1 illustrates an environment in which a fragrance dispensing system may be implemented.

FIG. 1 illustrates an exemplary environment 1 in which various embodiments of the present disclosure may be implemented. Environment 1 includes fragrance dispensing systems 100 (shown as 100A and 100B), input devices 12, 14, and 16, and network 10. Control signal 200 is transmitted from input devices 12, 14, and 16 over network 10 to fragrance dispensing systems 100. Network 10 represents generally any cable, wireless, or remote link that provides electronic communication between input devices 12, 14, 16 and fragrance dispensing system 100. Input devices 12, 14, and 16 represent generally any computing device capable of communicating with fragrance dispensing system 100. In some embodiments, input devices 12, 14, and 16 may be a touch screen interface on an exterior of fragrance dispensing system 100. In some embodiments, input devices 12, 14, and 16 may be a mobile computing device, such as a cellular phone, a tablet, a laptop, a desktop computer, or a combination thereof.

Figure 2:
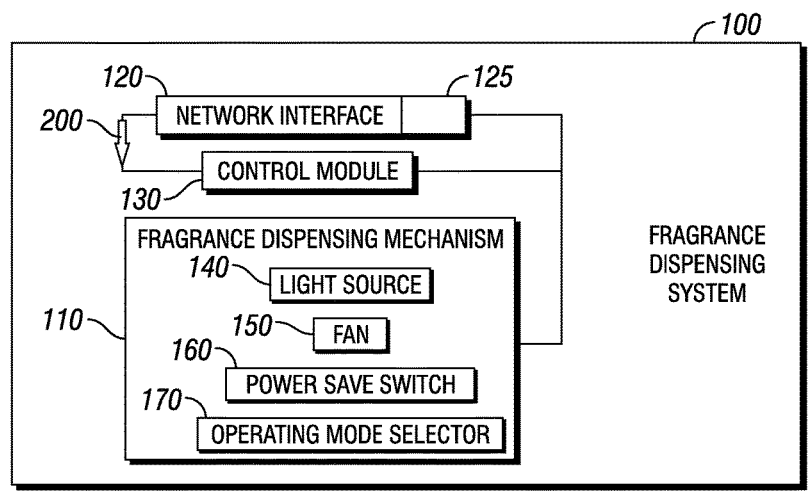
FIG. 2 is a block diagram of a fragrance dispensing system having a network interface, a control module, and a fragrance dispensing mechanism.

FIG. 2 shows a block diagram of fragrance dispensing system 100 having fragrance dispensing mechanism 110, network interface 120, and control module 130. Fragrance dispensing mechanism 110 is configured to dispense a fragrance into the surrounding air. Control module 130 is configured to control fragrance dispensing mechanism 110 as described herein. Control module 130 receives control signal 200 from input devices 12, 14, and 16 via network interface 120. Control module 130 may include a processor. The processor represents any combination of hardware and/or programming capable of carrying out instructions and interacting with components of fragrance dispensing system 100. Control signal 200 may include instructions to be executed by control module 130. Network interface 120 may include wireless interface 125 that receives a wireless signal from input devices 12, 14, and 16. In some embodiments, network interface 120 may communicate with a data network. For example, the wireless interface 125 may communicate via a point-to-point network, a local area network, a wide area network, a Bluetooth network, a Wi-Fi network, a cellular network, a cellular data network, a WiMAX network, a radio network, an infrared network, or a near-field communication network. In some embodiments, network interface 120 is integrated into a printed circuit board of control module 130. Network interface 120 may enable fragrance dispensing system 100 to be controlled from anywhere as long as control module 130 is connected to network 10. Input devices 12, 14, and 16 may access network 10 directly or indirectly. The indirect access may be through a modem or server. For example, an application installed on smart phone 14 may communicate with control module 130 connected to network 10 even if smart phone 14 is located in a different geographic region.

Input devices 12, 14, and 16 may include an application running on input devices 12, 14, and 16. The application may be obtained through various means, such as from an application store or downloaded directly from the internet. The application may be installed on input devices 12, 14, and 16 using various operating systems. For example, the application may be installed on a device running Windows, Linux, iOS, Android, or other operating systems. Input devices 12, 14, and 16 may include a processor. The processor represents any combination of hardware and/or programming that can be utilized by input devices 12, 14, and 16 to initialize and run the application, as described herein. Input devices 12, 14, and 16 may include local memory for storing user input 18. The processor may access user input 18 from the local memory and create control signal 200. Input devices 12, 14, and 16 may include a wireless transmitter to communicate control signal 200 directly to network 10. The wireless transmitter may be used to transmit control signal 200 as user input 18 is received at input devices 12, 14, and 16. The processor may generate interface 20 (shown in FIG. 5) of the application. User input 18 may be received at the application via interface 20. User input 18 may indicate a setting corresponding to fragrance dispensing system 100. Control signal 200 is generated based on user input 18. The application may then transmit control signal 200 to control module 130 of fragrance dispensing system 100 through network interface 120 and network 10. Control module 130 configures fragrance dispensing system 100 to the setting in response to control signal 200. By way of example, control module 130 and the application may be used with a SimpleScents® Fragrance Dispensing System sold by Harmony Brands LLC of Draper, Utah and described in U.S. patent application Ser. No. 14/517,776, filed on Oct. 17, 2014, and entitled "Decorative Fragrance Dispensing System," and in U.S. patent application Ser. No. 14/517,789, filed on Oct. 17, 2014 and entitled "Decorative Fragrance Dispensing System," both of which are hereby incorporated by reference in their entirety.

A non-transitory computer readable medium may store instructions that, when executed by the processor of the input devices 12, 14, and 16, causes the processor to generate interface 20 of the application, receive user input 18 via interface 20, and transmit control signal 200 to fragrance dispensing system 100 based on a setting indicated by user input 18.

As shown in FIGS. 1-2, the application may communicate with a plurality of control modules 130. Received user input 18 may indicate settings corresponding to different fragrance dispensing systems 100. Control signal 200 is transmitted to the plurality of control modules 130 of fragrance dispensing systems 100. The plurality of control modules 130 may be located in different locations and may control different models of fragrance dispensing systems 100 (shown as 100A and 100B). The different models may have different fragrance dispensing mechanisms 110. For example, some fragrance dispensing systems 100B may warm scented wax to distribute a fragrance and some fragrance dispensing systems 100A may use a fan to circulate air through a fragrance sachet. The application may communicate with the different control modules 130 separately or may communicate with a plurality of control modules 130 as a group. Control modules 130 configure their respective fragrance dispensing systems 100 to the settings in response to control signal 200.

Fragrance dispensing mechanism 110 may include light source 140 and fan 150. Some embodiments may include light source 140 without fan 150. Other embodiments may include fan 150 without light source 140. Light source 140 may emit light into the surrounding area and may provide ambient lighting for fragrance dispensing system 100. Light source 140 may include LEDs. The color and intensity of light source 140 may be adjustable. In some embodiments, light source 140 may assist in distributing a fragrance to the surrounding air. For example, light source 140 may produce heat and melt a fragrance device, such as a scented wax, to release a fragrance into the surrounding air. Fan 150 distributes fragrance into the surrounding air. For example, fan 150 may circulate air through a fragrance device, such as an ethylene vinyl acetate (EVA) bead pack, and into the surrounding air. Nevertheless, other materials and techniques for distributing fragrance may be used. Fan 150 may have an adjustable fan speed.

Fragrance dispensing system 100 may include operating mode selector 170, such as a knob or dial, for manually controlling features of fragrance dispensing system 100. Operating mode selector 170 may be a dial with four positions corresponding to different control settings. In the first position, fragrance dispensing system 100 is in a non-operating state—fan 150 and light source 140 are both in an off position. In other positions, fragrance dispensing system 100 is in an operating state. In the second position, fan 150 is in an off position and light source 140 is in an on position. In the third position, light source 140 is in an on position and fan 150 is operating at a low speed. In the fourth position, light source 140 is in an on position and fan 150 is operating at a high speed. In some embodiments, operating mode selector 170 may have positions corresponding only to settings of light source 140. In other embodiments, operating mode selector 170 may have positions corresponding only to settings of fan 150. Fragrance dispensing mechanism 110 may include power save switch 160, such as a toggle switch or button, that selects between a power save mode and a normal mode of fragrance dispensing system 100. In the power save mode, fragrance dispensing system 100 may be active for a first period of time and be inactive for a second period of time.

In an embodiment, control module 130 is connected to the application by first turning on fragrance dispensing system 100. This may be accomplished by manipulating operating mode selector 170. Once turned on, control module 130 and network interface 120 may automatically be activated and prepared for setup. For example, control module 130 having wireless interface 125 may enable a user to connect to a wireless network upon turning on fragrance dispensing system 100. Control module 130 may be connected to a secured or unsecured network. Control module 130 may be connected to network 10 through an interface on fragrance dispensing system 100, a Wi-Fi protected setup (WPS), or setup may be completed remotely through the application. The application may communicate with control module 130 of fragrance dispensing system 100 once setup has been completed. In some embodiments, fragrance dispensing system 100 may continue to be controlled manually through the use of operating mode selector 170 and/or power save switch 160 while also being controlled through the application. The application may notify a user through the application when manual control changes occur.

Figure 3:
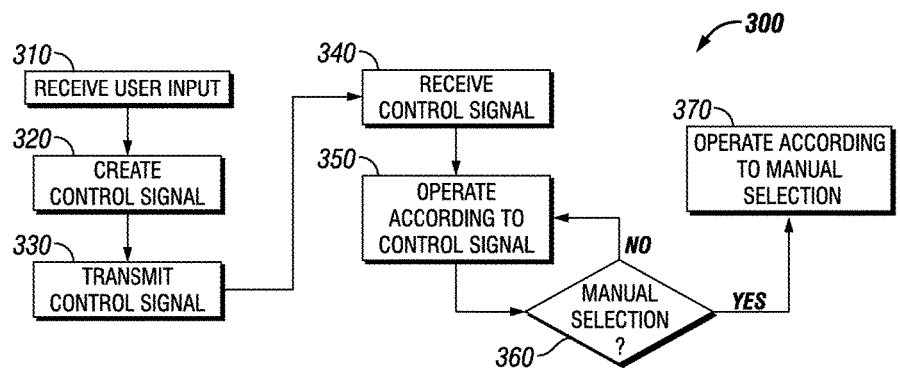
FIG. 3 shows a flow chart of a method of operating a fragrance dispensing system, according to an embodiment of the present disclosure.

After a user has installed the application and completed initial setup, the application may be used to control fragrance dispensing system 100. FIG. 3 shows one method 300 of operating fragrance dispensing system 100. In step 310, user input 18 is received at the application via interface 20 generated by the processor. In steps 320 and 330, control signal 200 is created from the received user input 18 and transmitted to network interface 120 of fragrance dispensing system 100. In step 340, network interface 120 receives control signal 200 and communicates control signal 200 with control module 130. Control module 130 controls fragrance dispensing mechanism 110 according to the commands of control signal 200 in step 350. In some embodiments, control module 130 continues to operate fragrance dispensing mechanism 110 in accordance with the commands of control signal 200 until a manual selection is made by a user in decision step 360. By way of example, the manual selection may be turning operating mode selector 170 on fragrance dispensing system 100 to another setting. Once a manual selection has been made by the user, step 370 includes control module 130 operating fragrance dispensing mechanism 110 in accordance with the manual selection made by the user. If additional user input 18 is received, method 300 is repeated.

Figure 4:
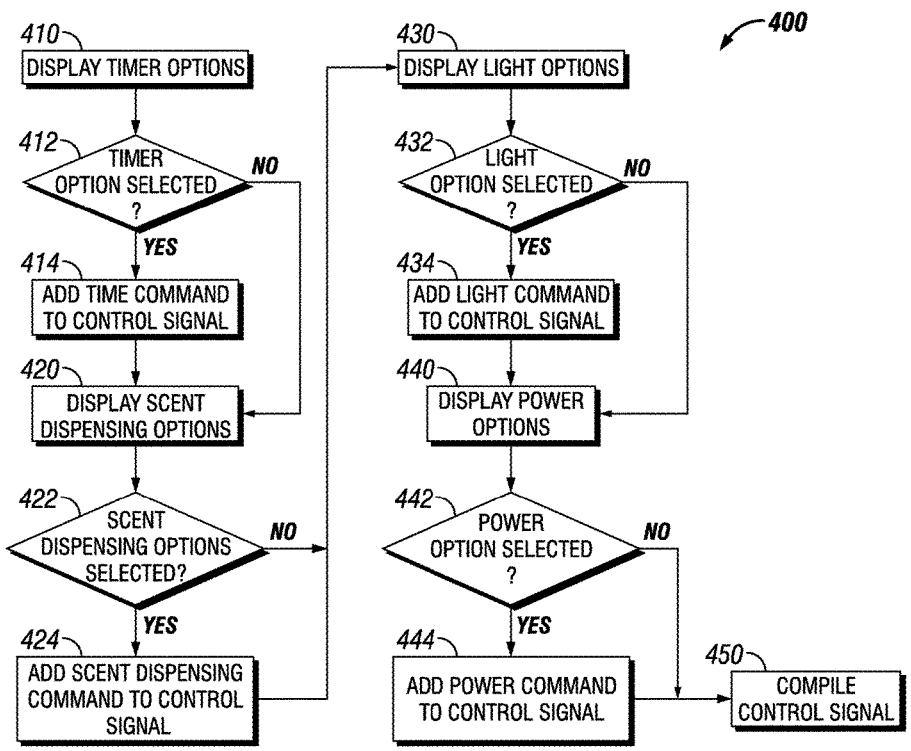
FIG. 4 shows a flow chart of a method of generating a control signal used to control a fragrance dispensing system, according to an embodiment of the present disclosure.

FIG. 4 shows one method 400 of generating control signal 200 to control fragrance dispensing system 100. In step 410, interface 20 displays selectable timer options to the user. The timer options correspond to a timer setting of fragrance dispensing system 100. In decision step 412, the user may indicate the timer options desired. If at least one timer option has been selected by the user, step 414 adds a time command to control signal 200. The time command indicates periods when control module 130 modifies or controls settings of fragrance dispensing system 100. A plurality of timer options may be selected by the user and correspond to a plurality of timer settings. Each timer setting may include a set of days and a time period corresponding to an operating state of fragrance dispensing system 100. In step 420, interface 20 displays selectable scent dispensing options to the user. The scent dispensing options may include fan speed control options corresponding to a fan speed setting of fan 150 of fragrance dispensing system 100. In decision step 422, the user may indicate the scent dispensing options desired. If at least one scent dispensing option has been selected by the user, step 424 adds a scent dispensing command to control signal 200.

In step 430, interface 20 displays selectable light control options to the user. The light control options correspond to a light source setting of light source 140 of fragrance dispensing system 100. The light control options may include colors, intensities, and patterns of light source 140. In decision step 432, the user may indicate the light control options desired. If at least one light option has been selected by the user, step 434 adds a light command to control signal 200. The light source control options may include a plurality of color control options corresponding to a plurality of color settings and a light intensity control option corresponding to a light intensity setting. The color setting and the light intensity setting may be part of the light source setting. In step 440, interface 20 displays selectable power options to the user. The power options correspond to power mode settings of fragrance dispensing system 100. The power mode settings may include an operating state, a non-operating state, a power saving state, or a combination thereof. In decision step 442, the user may indicate the power options desired. If at least one power option has been selected by the user, step 444 adds a power command to control signal 200. In step 450, control signal 200 is compiled using the applicable commands. Control signal 200 may be compiled using the processor of input devices 12, 14, and 16. Control signal 200 may comprise a command to operate according to a timer setting, a power mode setting, a fan speed setting, a light source setting, or a combination thereof.

Figure 5:
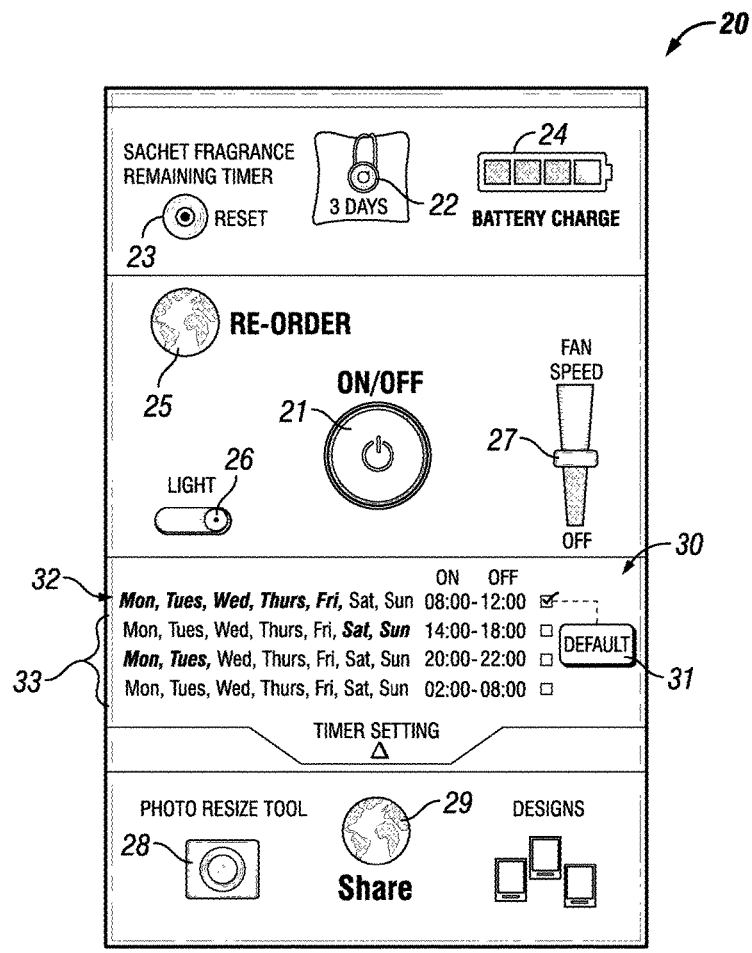
FIG. 5 shows an embodiment of an interface usable with embodiments of a fragrance dispensing system with a timer control in the default configuration.

FIG. 5 shows an embodiment of interface 20 of an application which receives user input 18 and controls fragrance dispensing system 100. User input 18 corresponds to a desired setting of fragrance dispensing system 100. Control signal 200 is created in response to the received user input 18 and corresponds to the desired settings. The application may then communicate control signal 200, and thus the desired settings, to network interface 120. Network interface 120 communicates control signal 200 to control module 130. Control module 130 adjusts the settings on fragrance dispensing system 100 to reflect the desired settings. Interface 20 displays options for controlling features of fragrance dispensing system 100. Interface 20 may include power button 21, light control 26, fan control 27, and timer control 30, or any combination thereof.

Power button 21 may be configured to control operating modes of fragrance dispensing system 100. The operating modes may include a non-operating mode, a normal mode, and a power saving mode. In the normal mode, fragrance dispensing system 100 may operate continuously. By way of example, power button 21 may cycle between operating modes each time power button 21 is pressed. In the power saving mode, fragrance dispensing system 100 may operate in a power saving state. For example, fragrance dispensing system 100 with fan 150 may run for fifteen minutes and turn off for five minutes. If timer control 30 is engaged, as discussed below, then fragrance dispensing system 100 may be operated in normal or power saving mode during those time periods determined by timer control 30. For example, during a first period of time, fan 150 may cycle between actuating airflow for a first duration and refraining from actuating airflow during a second duration. If timer control 30 is not engaged, then fragrance dispensing system 100 may continue to operate in normal or power savings mode until fragrance dispensing system 100 is turned off or the batteries require recharging. In some embodiments, power button 21 may override a previously indicated setting of operating mode selector 170.

Light control 26 may be configured to control characteristics of light source 140. Light control 26 may turn on and off, vary the intensity, color, and pattern, or a combination thereof, of light source 140. Light control 26 may be a slide control. Light source 140 may default to an off position.

Fan control 27 may be configured to control the operating speed of fan 150. Fan control 27 may be a slide control that allows a user to select an operating speed of fan 150 between stopped and full speed. Fan control 27 may include predetermined speeds or may be fully adjustable. Fan 150 may default to a low speed. In addition, the operating speed of fan 150 may be adjustable using operating model selector 170. Fan control 27 may override a previously indicated setting of operating mode selector 170. Subsequent use of operating mode selector 170 may override a previously indicated setting of fan control 27. For example, if the operating speed of fan 150 is adjusted using operating mode selector 170, fan control 27 may automatically return to its default position.

Figure 6:
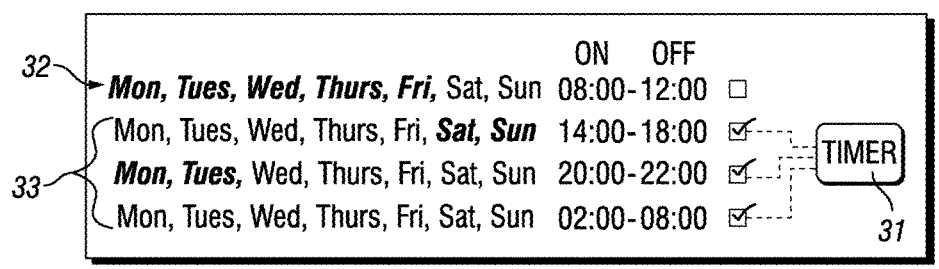
FIG. 6 shows a partial view of the interface of FIG. 5 with the timer options of the timer control selected.

Timer control 30 may be configured to affect the operation of fragrance dispensing system 100 within certain time periods. Timer control 30 has an engaged state and a disengaged state. In the disengaged state, timer control 30 does not affect the operation of fragrance dispensing system 100. For example, fragrance dispensing system 100 may continue to operate until it is turned off or the batteries require recharging. In the engaged state, fragrance dispensing system 100 operates during time periods determined by timer control 30. Timer control 30 may include timer button 31, default options 32, timer options 33, or a combination thereof. Timer button 31 may switch between default options 32 and timer options 33. At startup, default options 32 may be shown and may automatically be selected. For example, default options 32 may be for four hours each weekday as shown in FIG. 5. As shown in FIG. 6, timer options 33 may be selected by a user to indicate times at which fragrance dispensing system 100 is in an operating or non-operating state. A user may add additional timer options 33 to a list of available timer options 33 for the user to choose from. A user may select more than one timed setting 33. For example, as shown in FIG. 5, three different timer options 33 may be chosen. A drop-down menu may reveal timer control 30 when timer control 30 is being modified.

In some embodiments, timer control 30 may control other features of fragrance dispensing system 100. For example, timer control 30 may interact with fan control 27 such that the operating speed of fan 150 is modified during a time period determined by timer control 30. Fan 150 may operate at a low speed for a first time period and operate at a high speed for a second time period. Likewise, timer control 30 may interact with light control 26 such that the color, intensity, pattern, or a combination thereof, of light source 140 are modified during a time period determined by timer control 30.

Figure 7:
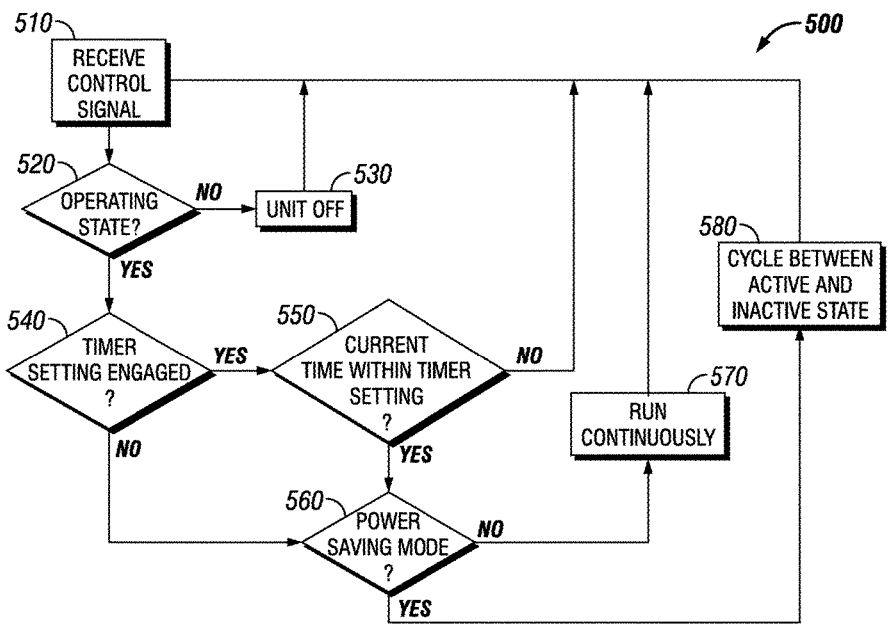
FIG. 7 shows a flow chart of a method of controlling a fragrance dispensing system, according to an embodiment of the present disclosure.

FIG. 7. shows one method 500 of controlling fragrance dispensing system 100 using timer control 30. In step 510, control signal 200 is received by fragrance dispensing system 100. Control signal 200 includes commands regarding periods for operation as determined by timer control 30. In decision step 520, control module 130 determines whether fragrance dispensing system 100 is in an operating state or a non-operating state. If fragrance dispensing system 100 is in a non-operating state, fragrance dispensing system 100 is determined to be off in step 530. Fragrance dispensing system 100 will remain in the non-operating state until control signal 200 includes a command to place fragrance dispensing system 100 in the operating state or operating mode selector 170 is used to place fragrance dispensing system 100 in the operating state. Once fragrance dispensing system 100 is in an operating state, decision step 540 determines whether timer control 30 is engaged or disengaged. If timer control 30 is engaged, decision step 550 determines whether the current time is within the period determined by timer control 30. If the current time is not within the period, no step is taken until the current time is within the period. Once the current time is within the period, or if time setting 30 is disengaged, decision step 560 determines whether fragrance dispensing system 100 is in the power save mode. If fragrance dispensing system 100 is not in the power save mode, fragrance dispensing system 100 will run continuously in step 570. If fragrance dispensing system 100 is in the power save mode, fragrance dispensing system 100 will cycle between an active state and an inactive state to preserve energy in step 580. Method 500 may continue to loop through decision steps 520, 540, 550, and 560 to determine if any parameters have changed.

As further shown in FIG. 5, interface 20 may include other features that indicate the operating status of fragrance dispensing system 100. Interface 20 may include fragrance level indicator 22, reset button 23, and battery indicator 24, or a combination thereof. Battery indicator 24 indicates the battery life remaining before a charge is needed. By way of example, the battery life remaining may be displayed as a numerical percentage. The battery life remaining may be displayed as a percentage of bars and may decrease as battery life is lessened.

Figure 8:
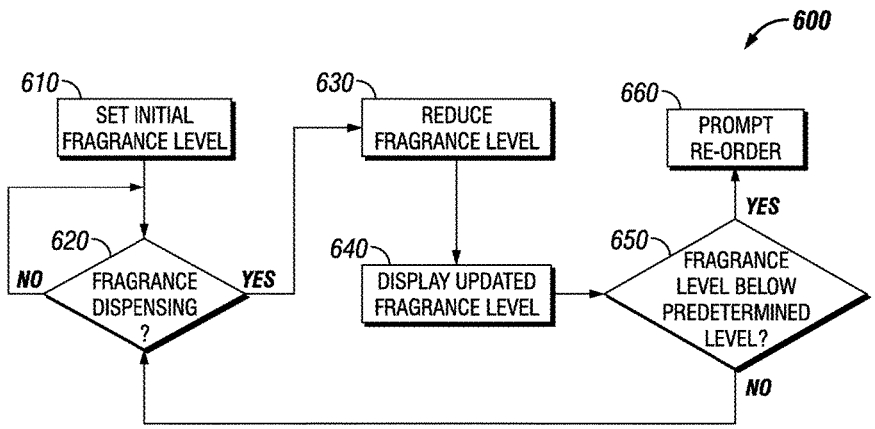
FIG. 8 shows a flow chart of a method of operating a fragrance level indicator, according to an embodiment of the present disclosure.

Fragrance indicator 22 indicates the length of time that a fragrance device has been in use or how much time remains before the fragrance is depleted. FIG. 8 shows one method 600 of operating fragrance level indicator 22. In step 610, an initial fragrance level is determined. The initial fragrance level may depend on the size and type of the fragrance device used in fragrance dispensing system 100. In decision step 620, it is determined whether fragrance is being dispensed by fragrance dispensing system 100. When a fragrance is dispensed, step 630 reduces the remaining fragrance level in accordance with the rigorousness of the use. For example, a high operating speed of fan 150 may deplete the fragrance level more quickly than a low operating speed. The remaining fragrance level is updated and displayed in step 640. In decision step 650, it is determined whether the remaining fragrance level is below a predetermined level. By way of example, the predetermined level may be 20% of the initial fragrance level. Once the remaining fragrance level has fallen below the predetermined level, step 660 prompts a user to re-order a replacement fragrance device. In some embodiments, a user may simply be notified that the fragrance level has fallen below the predetermined level. Reset button 23 may reset the initial fragrance level when a new fragrance source is supplied.

Interface 20 may include tools to assist users in operating their fragrance dispensing system 100. Interface 20 may include re-order tool 25, photo resize tool 28, and share tool 29, or a combination thereof. Re-order tool 25 is configured to link users to order replacement fragrance devices, such as bead packets, and may provide online links to retailers. Re-order tool 25 may integrate with fragrance level indicator 22 such that when the fragrance level drops below the predetermined level, re-order tool 25 is launched and a user is presented with compatible fragrance devices. Re-order tool 25 may also recommend fragrances that are popular within a selected geographic region or season. Various fragrance dispensing systems 100 positioned throughout a region may communicate information with a provider of fragrance dispensing systems 100. For example, the information may include the popular fragrances and fragrance dispensing system designs. Also for example, the information may include feedback from the control module, product information, user feedback, and other information used by retailers and providers to improve products, target a market, suggest similar products, or the like.

Photo resize tool 28 is configured to capture a photo of a particular setting. A user may select a design of a fragrance dispensing system, such as a SimpleScents® device, from a folder and may drag and resize the design to incorporate the design into the photo. For example, interface 20 may include a design folder containing all of the current SimpleScents® designs that can be viewed, dragged, and resized in the photos. Advantageously, a user may preview a design and appearance in a particular setting before purchasing it.

Share tool 29 is configured to enable a user to upload photos from photo resize tool 28 to an account on a social media website. Product information, such as the SimpleScents® design being used, may be included to assist viewers in identifying the design in the photo. The product information may include the specific fragrance dispensing system being used, the fragrance, and an online link to retailers.

The schematic diagrams of the figures illustrate exemplary environments in which embodiments of the present disclosure may be implemented. Implementation, however, is not limited to these environments. The diagrams of the figures show the architecture, functionality, and operation of various embodiments of the present disclosure. A number of the blocks are defined as programs. Each of those blocks may represent in whole or in part a module, segment, or portion of code that comprises one or more executable instructions to implement the specified logical function(s). Each block may represent a circuit or a number of interconnected circuits to implement the specified logical function(s).

Also, the present disclosure can be embodied in any computer-readable media for use by or in connection with an instruction execution system such as a computer/processor based system or an ASIC (Application Specific Integrated Circuit) or other system that can fetch or obtain the logic from computer-readable media and execute the instructions contained therein. "Computer-readable media" can be any media that can contain, store, or maintain programs and data for use by or in connection with the instruction execution system. Computer readable media can comprise any one of many physical media such as, for example, electronic, magnetic, optical, electromagnetic, or semiconductor media. More specific examples of suitable computer-readable media include, but are not limited to, a portable magnetic computer diskette such as floppy diskettes or hard drives, a random access memory (RAM), a read-only memory (ROM), an erasable programmable read-only memory, or a portable compact disc.

Although this disclosure has been described in terms of certain preferred embodiments, other embodiments that are apparent to those of ordinary skill in the art, including embodiments that do not provide all of the features and advantages set forth herein, are also within the scope of this disclosure. Accordingly, the scope of the present disclosure is defined only by reference to the appended claims and equivalents thereof.

What is claimed is:

1. A fragrance dispensing system comprising:
   a first fragrance dispensing mechanism and a second fragrance dispensing mechanism;
   a network interface;
   a fragrance indicator representing a fragrance level related to a fragrance device;
   a control module configured to receive a control signal from an input device via the network interface, the control signal being an electronic communication transmitted over a network from the input device to the fragrance dispensing system, the control signal indicating a first setting corresponding to the first fragrance dispensing mechanism and a second setting corresponding to the second fragrance dispensing mechanism, the control module controlling the first fragrance dispensing mechanism and the second fragrance dispensing mechanism according to one or more commands of the control signal, the control signal corresponding to settings of the first fragrance dispensing mechanism and the second fragrance dispensing mechanism; and
   a power save switch, wherein the control module determines a power mode based on a position of the power save switch, the power mode being selectable between a power save mode and a normal mode, the control module cycling between an active state and an inactive state in response to the control module determining that the power save switch is in power save mode, wherein the active state includes the control module performing the one or more commands of the control signal, and wherein the inactive state includes the control module controlling the first fragrance dispensing mechanism and/or the second fragrance dispensing mechanism to be inactive for a period of time.

2. The fragrance dispensing system of claim 1, wherein the first or second fragrance dispensing mechanism includes a fan, and wherein the control module determines a fan speed setting based on the control signal.

3. The fragrance dispensing system of claim 1, wherein the first or second fragrance dispensing mechanism includes a light source, and wherein the control module determines a light source setting based on the control signal.

4. The fragrance dispensing system of claim 3, wherein the light source setting includes a color setting, a light intensity setting, or a combination thereof.

5. The fragrance dispensing system of claim 1, wherein the control module determines a timer setting based on the control signal, the timer setting corresponding to a time period when the control module controls the first or second fragrance dispensing mechanism.

6. The fragrance dispensing system of claim 5, wherein the control module actuates airflow for a first duration during the time period and refrains from actuating airflow for a second duration during the time period while in the power save mode.

7. A fragrance dispensing system comprising:
   a first fragrance dispensing mechanism and a second fragrance dispensing mechanism;
   an interface configured to receive user input;
   a fragrance indicator representing a fragrance level related to a fragrance device;
   a control module configured to control the first fragrance dispensing mechanism and the second fragrance dispensing mechanism based on the user input as transmitted in one or more commands of a control signal, the user input corresponding to settings of the first fragrance dispensing mechanism and the second fragrance dispensing mechanism, the interface being configured to produce the control signal in response to the user input, the control signal being an electronic communication transmitted over a network from an input device to the fragrance dispensing system, the control signal indicating a first setting corresponding to the first fragrance dispensing mechanism and a second setting corresponding to the second fragrance dispensing mechanism, wherein the control module determines a timer setting based on the control signal, the timer setting corresponding to a time period when the control module controls the first or second fragrance dispensing mechanism; and
   a power save switch, wherein the control module determines a power mode based on a position of the power save switch, the power mode being selectable between a power save mode and a normal mode, the control module cycling between an active state and an inactive state in response to the control module determining that the power save switch is in power save mode, wherein the active state includes performing the one or more commands of the control signal and the inactive state includes inactivity for a period of time.

8. The system of claim 7, wherein the first or second fragrance dispensing mechanism includes a fan and a light source, and user input corresponding to a speed of the fan, a configuration of the light source, and a time period when the control module controls the speed of the fan and the configuration of the light source.

9. A fragrance dispensing system comprising:
   a fragrance dispensing mechanism;
   a network interface;
   a control module configured to receive a control signal from an input device via the network interface, the control module controlling the fragrance dispensing mechanism according to one or more commands of the control signal, the control signal corresponding to settings of the fragrance dispensing mechanism, the control signal being an electronic communication transmitted over a network from the network interface to the fragrance dispensing system, wherein the control module determines a timer setting based on the control signal, the timer setting corresponding to a time period when the control module controls the fragrance dispensing mechanism; and
   a power save switch, wherein the control module determines a power mode based on a position of the power save switch, the power mode being selectable between a power save mode and a normal mode.

10. The fragrance dispensing system of claim 9, wherein the fragrance dispensing mechanism includes a fan, and wherein the control module determines a fan speed setting based on the control signal.

11. The fragrance dispensing system of claim 9, wherein the fragrance dispensing mechanism includes a light source, and wherein the control module determines a light source setting based on the control signal.

12. The fragrance dispensing system of claim 11, wherein the light source setting includes a color setting, a light intensity setting, or a combination thereof.

13. The fragrance dispensing system of claim 9, wherein the control module actuates airflow for a first duration during the time period and refrains from actuating airflow for a second duration during the time period while in the power save mode.

* * * * *